United States Patent [19]

Anthony et al.

[11] Patent Number: 4,877,811
[45] Date of Patent: Oct. 31, 1989

[54] CHEMICAL COMPOUNDS

[75] Inventors: Vivienne M. Anthony, Maidenhead; John M. Clough, Marlow; Christopher A. Godfrey, Bracknell, all of United Kingdom

[73] Assignee: Imperial Chemical Industries PLC, London, Great Britain

[21] Appl. No.: 119,484

[22] Filed: Nov. 12, 1987

[30] Foreign Application Priority Data

Nov. 11, 1986 [DK] Denmark ............................. 4972/85
Dec. 3, 1986 [GB] United Kingdom ................ 8628923

[51] Int. Cl.$^4$ ..................... C07C 121/64; C07C 69/76; A01N 37/34; A01N 37/36
[52] U.S. Cl. ................................. 514/522; 514/105; 514/107; 514/111; 514/532; 514/539; 546/342; 544/335; 549/79; 549/501; 560/21; 560/56
[58] Field of Search ...................... 560/56, 21; 514/532, 514/539, 522; 558/414

[56] References Cited

U.S. PATENT DOCUMENTS

| 2,722,542 | 11/1955 | Rexford | 560/56 X |
| 2,824,121 | 2/1958 | Nicholl et al. | 560/56 X |
| 3,828,033 | 8/1974 | Nelson | 560/56 X |
| 3,896,157 | 7/1975 | Fried et al. | 560/56 X |
| 4,709,078 | 11/1987 | Schirmer et al. | 560/12 X |
| 4,723,034 | 2/1988 | Schirmer et al. | 560/9 X |

FOREIGN PATENT DOCUMENTS 8700356 9/1987 Netherlands ......................... 560/56

OTHER PUBLICATIONS

J. Chem. Soc., (1962), pp. 3828–3830, Arison et al.
CA;97:197996m, (1982), Englaender et al.
CA;57:13321e, (1962), Arison et al.
CA;105:78670z, (1986), Bushell et al.

Primary Examiner—Joseph P. Brust
Attorney, Agent, or Firm—Cushman, Darby & Cushman

[57] ABSTRACT

Compounds of the formula:

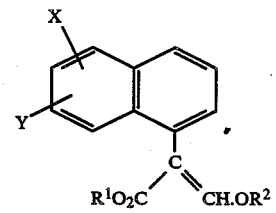

and stereoisomers thereof wherein X and Y, which are the same or different, are hydrogen, halogen, optionally substituted alkyl, optionally substituted cycloalkyl, optionally substituted cycloalkylalkyl, optionally substituted alkenyl, optionally substituted alkynyl, optionally substituted aryl, optionally substituted heteroaryl, optionally substituted alkoxy, optionally substituted aryloxy, optionally substituted heteroaryloxy, optionally substituted arylalkoxy, optionally substituted heteroarylalkoxy, optionally substituted acyloxy, optionally substituted amino, acylamino, nitro, cyano, —$CO_2R^3$, —$CONR^4R^5$, or —$COR^6$, except that X and Y are not both hydrogen; $R^1$ and $R^2$, which are the same or different, are alkyl or fluoroalkyl; and $R^3$, $R^4$, $R^5$ and $R^6$, which are the same or different, are hydrogen, alkyl, alkenyl, alkynyl, optionally substituted aryl, optionally substituted aralkyl, or cycloalkylalkyl.

The compounds are useful in agriculture, especially as fungicides but also as plant growth regulators, insecticides and miticides.

6 Claims, No Drawings
}

CHEMICAL COMPOUNDS

This invention relates to derivatives of propenoic acid useful in agriculture (especially as fungicides but also as plant growth regulators, insecticides and miticides), to processes for preparing them, to agricultural (especially fungicidal) compositions containing them, and to methods of using them to combat fungi (especially fungal infections in plants), to regulate plant growth and to control or kill insect and mite pests.

The invention provides a compound having the general formula (I):

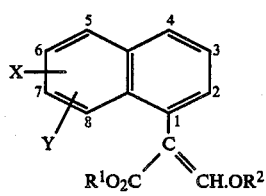

and stereoisomers thereof, wherein X and Y, which are the same or different, are hydrogen, halogen (fluorine, chlorine, bromine or iodine), optionally substituted alkyl, optionally substituted cycloalkyl, optionally substituted cycloalkylalkyl, optionally substituted alkenyl, optionally substituted alkynyl, optionally substituted aryl, optionally substituted heteroaryl, optionally substituted alkoxy (for example, haloalkoxy), optionally substituted aryloxy, optionally substituted heteroaryloxy, optionally substituted arylalkoxy, optionally substituted heteroarylalkoxy, optionally substituted acyloxy, optionally substituted amino, acylamino, nitro, cyano, —$CO_2R^3$, —$CONR^4R^5$, or —$COR^6$, except that X and Y are not both hydrogen; $R^1$ and $R^2$, which are the same or different, are alkyl (especially methyl) or fluoroalkyl (such as fluoromethyl, difluoromethyl or trifluoromethyl); and $R^3$, $R^4$, $R^5$ and $R^6$, which are the same or different, are hydrogen, alkyl, alkenyl, alkynyl, optionally substituted aryl, optionally substituted aralkyl, or cycloalkylalkyl.

The compounds of the invention contain at least one carbon-carbon double bond, and are sometimes obtained in the form of mixtures of geometric isomers. However, these mixtures can be separated into individual isomers, and this invention embraces such isomers.

The individual isomers which result from the unsymmetrically substituted double bond of the acrylate group are hereinafter identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq).

The compounds of this invention include those which are predominantly in the form of the Z-isomer and also those which are predominantly in the form of the E-isomer. In the present invention, the E-isomer is usually more fungicidal than the Z-isomer and forms a preferred embodiment.

Alkyl groups can be in the form of straight or branched chains, and preferably contain 1 to 6 carbon atoms, more preferably 1 to 4 carbon atoms. Examples are methyl, ethyl, propyl, (n- or iso-propyl) and butyl (n-, sec-, iso- or t-butyl). The methyl group is the preferred alkyl group for both $R^1$ and $R^2$.

Examples of X, Y, $R^3$, $R^4$, $R^5$ and $R^6$ when they are optionally substituted aryl groups are phenyl; 2-, 3- or 4-fluorophenyl; 2-, 3- or 4-chlorophenyl; 2,4-dichlorophenyl; 2,3-dichlorophenyl; 3,5-dichlorophenyl; 3,4-dichlorophenyl; 2,6-difluorophenyl; 3-methoxyphenyl; 4-methylphenyl; 3-phenylphenyl; 3-nitrophenyl; and 4-cyanophenyl. Examples of X and Y when they are optionally substituted heteroaryl groups are 2-, 3- or 4-pyridyl; 2, 4- or 5-pyrimidinyl; 2- or 3-pyrrolyl; 2- or 3-thienyl; 2- or 3-furyl; and 1-, 3- or 4-(1,2,4-triazolyl); each optionally substituted with one or more atoms or groups such as fluorine, chlorine, bromine, methyl, methoxy, trifluoromethoxy or cyano.

Of particular interest are compounds of the formula (V):

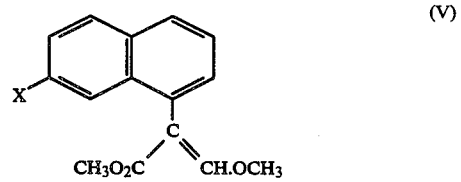

wherein X is optionally substituted aryl (especially phenyl) or optionally substituted heteroaryl (especially pyridyl, pyrimidinyl or thienyl). When X is substituted phenyl, preferred substituents, of which there may be one or more (usually one or two; either the same or different), are halogen (especially fluorine or chlorine), $C_{1-4}$ alkyl (especially methyl), $C_{1-4}$ alkoxy (especially methoxy), phenyl, nitro and cyano. Examples are given earlier. When X is subsituted heteroaryl, preferred substituents, of which there may be one or more (either the same or different) are halogen (especially fluorine, chlorine or bromine) $C_{1-4}$ alkyl (especially methyl), trifluoromethyl, $C_{1-4}$ alkoxy (especially methoxy), trifluoromethoxy and cyano. Examples are given earlier.

The invention is illustrated by the compounds presented in Table I below. In Table I, $R^1$ and $R^2$ are both methyl groups, and the alkoxypropenoate group has the E-geometry throughout.

TABLE I

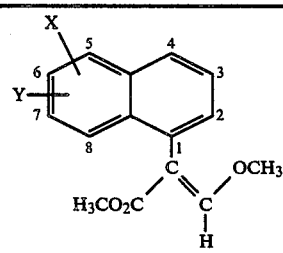

| COMPOUND NO. | X | Y | MELTING POINT (°C.) |
|---|---|---|---|
| 1 | 7-$C_6H_5$ | H | 106-107 |
| 2 | 6-$C_6H_5$ | H | |
| 3 | 6-(4-Cl—$C_6H_4$) | H | |
| 4 | 7-(4-Cl—$C_6H_4$) | H | |
| 5 | 7-(3-Cl—$C_6H_4$) | H | |
| 6 | 7-(2-Cl—$C_6H_4$) | H | |
| 7 | 7-(2-F—$C_6H_4$) | H | |
| 8 | 7-(2-F,3-Cl—$C_6H_3$) | H | |
| 9 | 7-(3-$CH_3O$,4-F—$C_6H_3$) | H | |
| 10 | 7-(3-$CH_3$,4-Cl—$C_6H_3$) | H | |
| 11 | 7-(3-Cl,4-F—$C_6H_3$) | H | |
| 12 | 6-Cl | 7-$C_6H_5$ | |
| 13 | 6-F | 7-$C_6H_5$ | |

TABLE I-continued (I)

[Structure: naphthalene with X at position 5-6, Y at position 6-7, and at C1 a substituent =C(CO2CH3)-C(H)=OCH3 roughly; the structure shows naphthalene ring with positions 2,3,4,5,6,7,8 labeled, X shown at position 5/6, Y at position 6/7, and C1 connected to C(=CH-OCH3)(CO2CH3)]

| COMPOUND NO. | X | Y | MELTING POINT (°C.) |
|---|---|---|---|
| 14 | 6-C$_6$H$_5$ | 7-F | |
| 15 | 7-(t-C$_4$H$_9$) | H | |
| 16 | 7-(n-C$_4$H$_9$) | H | |
| 17 | 7-(3-CH$_3$O—C$_6$H$_4$) | H | |
| 18 | 7-C$_6$H$_5$ | 8-F | |
| 19 | 5-F | 7-C$_6$H$_5$ | |
| 20 | 5-CH$_3$ | 7-C$_6$H$_5$ | |
| 21 | 7-(3,CF$_3$O—C$_6$H$_4$) | H | |
| 22 | 7-(2-pyridyl) | H | |
| 23 | 7-(3-pyridyl) | H | |
| 24 | 7-(4-pyridyl) | H | |
| 25 | 7-(2-thienyl) | H | |
| 26 | 7-(3-thienyl) | H | |
| 27 | 7-(2-pyrimidinyl) | H | |
| 28 | 7-(4-pyrimidinyl) | H | |
| 29 | 7-(5-pyrimidinyl) | H | |
| 30 | 7-[2-(5-CF$_3$—pyridyl)] | H | |
| 31 | 6-F | 7-(2-pyridyl) | |
| 32 | 7-(2-furyl) | H | |
| 33 | 7-(3-furyl) | H | |
| 34 | 7-[2-(5-Cl—thienyl)] | H | |

The compounds of the invention having the general formula (I) can be prepared from naphthylacetates of general formula (III) by the steps shown in Scheme I. Throughout Scheme I the terms R$^1$, R$^2$, X and Y are as defined above, and R$^3$ is hydrogen or a metal (such as sodium or potassium).

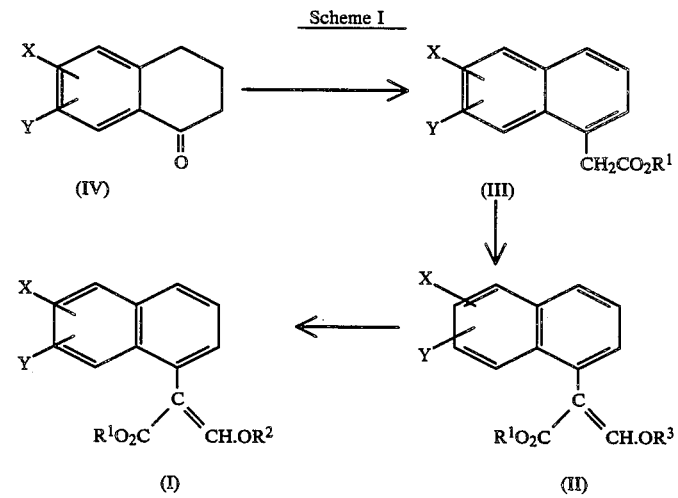

Scheme I

Thus compounds of general formula (I) can be prepared by treatment of naphthylacetates of general formula (III) with a base (such as sodium hydride or a sodium alkoxide) and a formic ester of the formula, HCO$_2$R$^1$ (such as methyl formate) in a suitable solvent. If a species of general formula R$^2$L, wherein L is a leaving group (such as a halide or R$^2$SO$_4$ anion), is then added to the reaction mixture, compounds of general formula (I) may be obtained. If a protic acid is added to the reaction mixture, compounds of general formula (II) wherein R$^3$ is hydrogen are obtained. Alternatively, the species of general formula (II) wherein R$^3$ is a metal (such as sodium) may itself be isolated from the reaction mixture.

Compounds of general formula (II) wherein R$^3$ is a metal atom can be converted into compounds of general formula (I) by treatment with a species of general formula R$^2$L, wherein L is as defined above, in a suitable solvent. Compounds of general formula (II) wherein R$^3$ is hydrogen can be converted into compounds of general formula (I) by successive treatments with a base (such as potassium carbonate or sodium hydride) and a species of general formula R$^2$L, in a suitable solvent.

Naphthylacetates of general formula (III) can be prepared by methods described in the chemical literature. For example, they can be prepared from alpha-tetralones of general formula (IV) by a Reformatskii reaction followed by dehydration and aromatisation (see, for example, J. S. Kaltenbronn, *J. Med. Chem.*, 1977, 20, 596).

In further aspects, the invention includes the processes hereinbefore described for preparing the compounds of the invention and the intermediate compounds having the formulae (II) and (III) used therein.

The compound of the invention are active fungicides, and may be used to control one or more of the diseases:

*Pyricularia oryzae* on rice.

*Puccinia recondita, Puccinia striiformis* and other rusts on wheat, *Puccinia hordei, Puccinia striiformis* and other rusts on barley, and rusts on other hosts eg. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (eg. cucumber), *Podosphaera leucotricha* on apples and *Uncinula necator* on vines.

*Pseudocercosporella herpotrichoides* on wheat.

*Cercospora arachidicola* and *Cercosporidium personata* on peanuts and other *Cercospora* species on other hosts for example sugar beet, bananas, soya beans and rice.

*Botrytiis cinerea* (grey mould) on tomatoes, strawberries, vegetables, vines and other hosts.

*Alternaria* species on vegetables (e.g. cucumber), oil seed rape, apples, tomatoes and other hosts.

*Venturia inaequalis* (scab) on apples.

*Plasmopara viticola* on vines.

Other downy mildews such as *Bremia lactucae* on lettuce, *Peronospora* spp. on soybeans, tobacco, onions and other hosts. *Pseudoperonospora humuli* on hops and *Pseudoperonospora cubensis* on cucurbits.

*Phytophthora infestans* on potatoes and tomatoes and other

*Phytophthora* spp. on vegetables, strawberries, avocado, pepper, ornamentals, tobacco, cocoa and other hosts.

Compound 1 has shown a broad range of activities against fungi in vitro.

Therefore in another aspect the invention provides a method of combating fungi which comprises applying to a plant, to a seed of a plant or to the locus of the plant or seed a fungicidally effective amount of a compound of formula (I) as hereinbefore defined, or a composition containing the same.

The compounds may also be useful as industrial (as opposed to agricultural) fungicides, eg. in the prevention of fungal attack on wood, hides, leather and especially paint films.

Some compounds may exhibit plant growth regulating activity and may be deployed for this purpose at appropriate rates of application.

Thereafter, in yet another aspect of the invention provides a method of regulating plant growth which comprises applying to a plant, to a seed of a plant or to the locus of the plant or seed an effective amount of a plant growth regulating compound of formula (I).

The compounds of the invention may also have useful insecticidal activity against a range of insect species and mites. Therefore in a further aspect of the invention there is provided a method of killing or controlling insect and mite pests which comprises administering to the pest or to a locus thereof an effective amount of an insecticidal or miticidal compound of formula (I).

The compounds may be used directly for agricultural purposes but are more conveniently formulated into compositions using a carrier or diluent. The invention thus provides a fungicidal, plant growth regulator, insecticidal or miticidal composition comprising a compound of general formula (I) as hereinbefore defined, and an acceptable carrier or diluent therefor.

As fungicides or plant growth regulators, the compounds can be applied in a number of ways. For example they can be applied, formulated or unformulated, directly to the foliage of a plant, to seeds or to other medium in which plants are growing or are to be planted. They can be sprayed on, dusted on or applied as a cream or paste formulation; or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition.

The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, eg. fluorotrichloromethane and dichlorodifluoromethane.

The invention compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salt of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carb-oxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, eg. compounds having similar or complementary fungicidal activity or which possess plant growth regulating, herbicidal or insecticidal activity.

A fungicidal compound which may be present in the composition of the invention may be one which is capable of combating ear diseases of cereals (eg. wheat) such as *Septoria*, *Gibberella* and *Helminthosporium* spp., seed and soil borne diseases and downy and powdery mildews on grapes and powdery mildew and scab on apple etc. By including another fungicide the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidone, vinclozolin, penconazole, myclobutanil, RO151297, S3308, pyrazophos, ethirimol, ditalimfos, tridemorph, triforine, nuarimol, triazbutyl, guazatine, triacetate salt of 1,1'-iminodi(octamethylene)diguanidine, propiconazole, prochloraz, flutriafol, hexaconazole ie. the chemical 1-(1,2,4-triazol-1-yl)-2-(2,4-dichlorophenyl)-hexan-2-ol, (2RS, 3RS)-2-(4-chlorophenyl)-3-cyclopropyl-1-(1H-1,2,4-triazol-1-yl)-butan-2-ol, (RS)-1-(4-chlorophenyl)-4,4-dimethyl-3-(1H-1,2,4-triazol-1-yl-methyl)pentan-3-ol, DPX H6573(1-(bis-4-fluorophenyl)methylsilyl)methyl)-1H-1,2,4-triazole, triadimefon, triadimenol, diclobutrazol, fenpropimorph, pyrifenox, fenpropidin, chlorozolinate, diniconazol, imazalil, fenfuram, carboxin, oxycarboxin, methylfuroxam, dodemorph, BAS 454, blasticidin S, Kasugamycin, edifenphos, kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyiminoacetyl)-3-ethyl urea, fenapanil, tolclofosmethyl, puroxyfur, polyram, maneb, mancozeb, captafol, chlorothalonil, anilazine, thiram, captan, folpet, zineb, propineb, sulphur, dinocap, binapacryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (eg. grasses).

Examples of suitable plant growth regulating compounds for use with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorofluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (eg. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, fenpentezol, inabenfide, triapenthenol and tecnazene.

The following Examples illustrate the invention. Throughout the Examples, the term 'ether' refers to diethyl ether, magnesium sulphate was used to dry solutions, and solutions were concentrated under reduced pressure. Reactions involving water-sensitive intermediates were performed under an atmosphere of nitrogen and solvents were dried before use, where appropriate. Unless otherwise stated, chromatography was performed on a column of silica gel as the stationary phase.

Where shown, infrared and n.m.r. data are selective; no attempt is made to list every absorption in all cases. $^1$H n.m.r. spectra were recorded at 270 MHz using CDCl$_3$-solutions unless otherwise stated. The following abbreviations are used throughout:

| THF = tetrahydrofuran | s = singlet |
| DMF = N,N—dimethylformamide | d = doublet |
| n.m.r. = nuclear magnetic resonance | t = triplet |
| IR = infrared | m = multiplet |
| m.p. = melting point | br = broad |

EXAMPLE 1

This Example illustrates the preparation of (E)-methyl 3-methoxy-2-(7-phenylnaphth-1-yl)propenoate (1); Compound No. 1 of Table I.

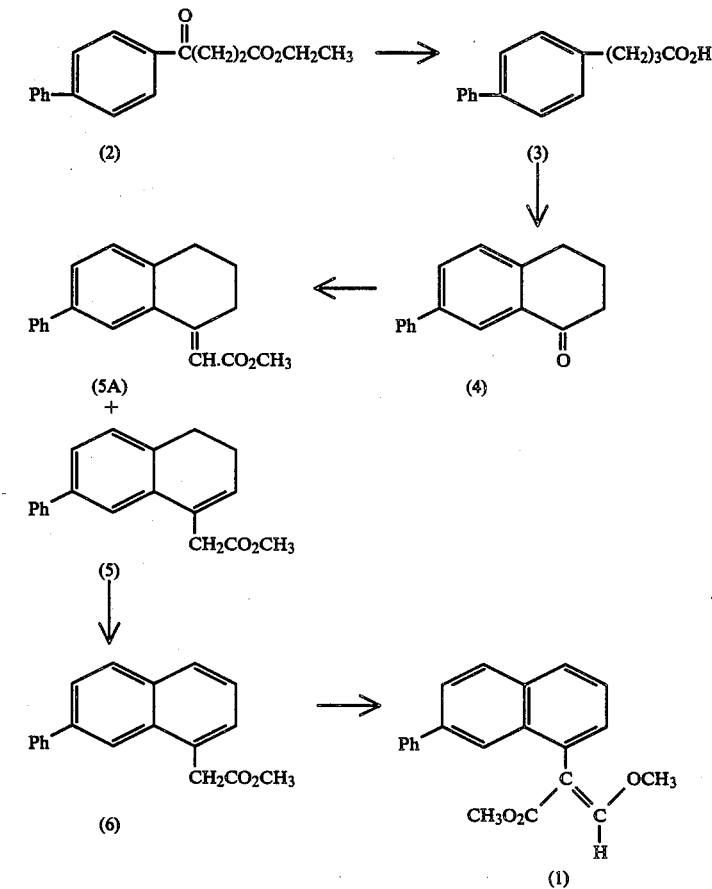

A mixture of biphenyl (50.0 g) and succinic anhydride (35.7 g) was added slowly in portions to a stirred solution of aluminium chloride (86.7 g) in nitrobenzene (300 ml). When the addition was complete, the stirred mixture was heated at 100° C. for 2½ hours, then allowed to stand overnight at room temperature. The nitromethane was removed by steam distillation and the solid residue was added carefully with vigorous stirring to an ice-cooled mixture of water (100 ml) and concentrated hydrochloric acid (100 ml). The solid which did not dissolve (59.9 g) was separated and the aqueous acidic layer was extracted with ethyl acetate. The extracts were dried and concentrated to give further yellow solid (11.2 g). The two batches of solids were combined and dissolved in hot ethanol. On cooling, crystals formed in this solution and they were filtered off and dried to give ethyl 3-(4-phenylbenzoyl)propanoate [(2), 28.9 g, 32% yield] as yellow flakes, IR (nujol): 1724, 1672 cm$^{-1}$. (Compare method of D. H. Hey and R. Wilkinson, J. Chem. Soc., 1940, 1030).

Triethylsilane (32.62 ml) was added in one portion to a stirred solution of ethyl 3-(4-phenylbenzoyl)propanoate [(2), 25.06 g] in trifluoroacetic acid (71.5 ml) and the resulting mixture was stirred at room temperature for about 20 hours. The resulting clear dark orange solution was diluted with water and extracted with ether. The extracts were washed with aqueous sodium bicarbonate (x2) and then water (x2), dried and concentrated to give a mobile brown liquid. Triethylsilane remaining in this liquid was removed by Kugelrohr evaporative distillation at 110° C. and a pressure of ca. 1 mmHg to leave crude ethyl 4-(4-phenylphenyl)butanoate (21.20 g) as a brown oil. (Compare method of C. T. West, S. J. Donnelly, D. A. Kooistra and M. P. Doyle, J. Org. Chem., 1973, 38, 2675).

A solution of ethyl 4-(4-phenylphenyl)butanoate (21.0 g) and potassium hydroxide (9.65 g) in ethanol (50 ml) and water (50 ml) was heated under reflux for 2 hours. The resulting mixture was allowed to cool, diluted with water (150 ml), washed with ether (x2), acidified with concentrated hydrochloric acid, and extracted with ether. The extracts were washed with water, dried and concentrated to give crude 4-(4-phenylphenyl)-butanoic acid [(3), 18.28 g] as a white solid, m.p. 111°–113° C. (D. H. Hey and R. Wilkinson, J. Chem.

Soc., 1940, 1030, give a m.p. of 118°–119° C. for this acid).

A mixture of 4-(4-phenylphenyl)butanoic acid (17.23 g) and thionyl chloride (200 ml) was heated under reflux for 1 hour. The excess thionyl chloride was removed under reduced pressure, and the residue was dissolved in dry dichloromethane and again concentrated under reduced pressure. A solution of the resulting acid chloride in dry dichloromethane (100 ml) was cooled to −78° C. and trifluoromethanesulphonic acid (6.98 ml) was added dropwise with stirring. After 15 minutes, the reaction mixture was allowed to warm to room temperature and stand for about 16 hours. It was poured into water and the aqueous and organic layers were separated. The aqueous layer was extracted with further dichloromethane and the combined organic layers were washed successively with sodium bicarbonate and water, dried and concentrated to give a viscous yellow oil (13.08 g). Chromatography using ether and petrol (1:1) as eluant gave the phenyltetralone (4) [7.87 g, 43% yield from ethyl 3-(4-phenylbenzoyl)propanoate (2)] as a pale yellow solid, m.p. 72°–74° C. (D. H. Hey and R. Wilkinson, J. Chem. Soc., 1940, 1030, give a m.p. of 69° C. for this phenyltetralone).

A solution of phenyltetralone [(4), 6.23 g] and methyl bromoacetate (3.23 ml) in ether (40 ml) was added dropwise to a stirred suspension of zinc powder (3.72 g) in dry THF (40 ml). During the addition, the reaction mixture was warmed with a stream of hot air until an exothermic reaction began, and then allowed to stir at room temperature for 30 minutes after the exothermic reaction had subsided. The reaction mixture was diluted with water and acidified with concentrated hydrochloric acid. The organic and aqueous layers were separated and the aqueous layer was extracted with further ether. The combined organic layers were washed with water (x2), dried and concentrated to give a yellow liquid. The liquid was heated on a steam bath with formic acid (ca. 60 ml) for 15 minutes, allowed to cool, diluted with water and extracted with ether. The extracts were washed with aqueous sodium bicarbonate then dried and concentrated to give a light brown oil (7.01 g). Chromatography using 20% ether in petrol as eluant gave the ester [(5), 5.5 g, 70% yield], $^1$H n.m.r.: delta 2.34 (2H, m), 2.83 (2H, t), 3.30 (2H, s), 3.68 (3H, s), 6.04 (1H, t), 7.17–7.6 (8H, m) p.p.m. and the regioisomeric ester [(5A), 1.1 g, 14% yield], a single stereoisomer. (Compare method of J. S. Kaltenbronn, J. Med. Chem., 1977, 20, 596).

A mixture of the ester [(5), 3.80 g] and sulphur (0.48 g) was heated at 220° C. for 3½ hours then allowed to cool. The resulting solid was partitioned between ether and water, and the aqueous layer was extracted with further ether. The combined ether layers were treated with magnesium sulphate and charcoal, filtered, concentrated and chromatographed using 25% ether in petrol as eluant to give the phenylnaphthalene [(6), 2.84 g, 75% yield] as a light brown oil, $^1$H n.m.r.: delta 3.68 (3H, s), 4.12 (2H, s), 7.4–7.6 (5H, m), 7.7–7.9 (4H, m), 8.0 (1H, d), 8.25 (1H, br s) p.p.m. (Compare method of J. S. Kaltenbronn, J. Med. Chem., 1977, 20, 596).

A solution of the phenylnaphthalene [(6), 3.0 g] in methyl formate (6.7 ml) and DMF (ca. 20 ml) was added dropwise to a stirred suspension of sodium hydride (0.52 g) in DMF (ca. 30 ml) cooled to about 0° C. Effervescence and foaming built up during the addition, and, when this subsided, the reaction mixture was allowed to warm to room temperature and stirred for 3½ hours. The mixture was diluted with water, acidified with concentrated hydrochloric acid, and extracted with ether. The extracts were washed with water (x2), dried and concentrated to give a yellow oil. Potassium carbonate (0.38 g) and dimethyl sulphate (1.03 ml) were added successively to a stirred solution of this yellow oil in DMF (ca. 30 ml). After 2 hours, the resulting mixture was diluted with water and extracted with ether. The extracts were washed with water, dried, concentrated and chromatographed using 30% ether in petrol as eluant to give a white solid (1.78 g). Crystallisation of this solid from a mixture of ether and petrol gave the title compound [(1), 1.21 g, 35% yield from the phenylnaphthalene (6)] as a white crystalline solid, m.p. 106°–107° C., $^1$H n.m.r.: delta 3.64 (3H, s), 3.78 (3H, s), 7.33–7.39 (2H, m), 7.40–7.52 (3H, m), 7.63–7.68 (2H, m), 7.72 (1H, dd), 7.80 (1H, s), 7.84 (1H, d), 7.89–7.94 (2H, m) p.p.m.

EXAMPLE 2

An emulsifiable concentrate is made up by mixing the ingredients, and stirring the mixture until all the constituents are dissolved.

| | |
|---|---|
| Compound of Example 1 | 10% |
| Isophorone | 25% |
| Calcium dodecylbenzenesulphonate | 5% |
| Nonylphenolethoxylate (13 moles ethylene oxide) | 10% |
| Alkyl benzenes | 50% |

EXAMPLE 3

The active ingredient is dissolved in methylene dichloride and the resultant liquid sprayed onto the granules of attapulgite clay. The solvent is then allowed to evaporate to produce a granular composition.

| | |
|---|---|
| Compound of Example 1 | 5% |
| Attapulgite granules | 95% |

EXAMPLE 4

A composition suitable for use as a seed dressing is prepared by grinding and mixing the three ingredients.

| | |
|---|---|
| Compound of Example 1 | 50% |
| Mineral oil | 2% |
| China clay | 48% |

EXAMPLE 5

A dustable powder is prepared by grinding and mixing the active ingredient with talc.

| | |
|---|---|
| Compound of Example 1 | 5% |
| Talc | 95% |

EXAMPLE 6

A suspension concentrate is prepared by ball milling the constituents below, to form an aqueous suspension of the ground mixture with water.

| | |
|---|---|
| Compound of Example 1 | 40% |
| Sodium lignosulphonate | 10% |
| Bentonite clay | 1% |
| Water | 49% |

This formulation can be used as a spray by diluting into water or applied directly to seed.

EXAMPLE 7

A wettable powder formulation is made by mixing and grinding together the ingredients below.

| | |
|---|---|
| Compound of Example 1 | 25% |
| Sodium lauryl sulphate | 2% |
| Sodium lignosulphonate | 5% |
| Silica | 25% |
| China clay | 43% |

EXAMPLE 8

Compound No. 1 was tested against a variety of foliar fungal diseases of plants. The technique employed was as follows.

The plants were grown in John Innes Potting Compost (No 1 or 2) in 4 cm diameter minipots. The test compound was formulated by bead milling with aqueous Dispersol T and diluted to the required concentration immediately before use. For the foliage diseases, the formulations (100 ppm active ingredient), were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (root drench) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace—5% of disease on untreated plants
2=6–25% of disease on untreated plants
1=26–59% of disease on untreated plants
0=60–100% of disease on untreated plants
The results are shown in Table II.

EXAMPLE 9

This Example illustrates the plant growth regulating properties of Compound 1 when tested on a whole plant screen against two species of plant. The plant species are identified in Table III with the leaf stage at which they were sprayed.

A formulation of Compound 1 was applied at 4000 ppm (4 kg/ha in a 1000 l/ha field volume) using a tracksprayer and a SS8004E (Teejet) nozzle.

After spraying, the plants were grown in a glasshouse with 25° C. day/22° C. night temperature. Supplementary lighting was supplied when necessary to provide an average photoperiod of 16 hours (14 hours minimum).

After 2–6 weeks in the glasshouse, depending on species and time of year, the plants were visually assessed for morphological characteristics against a control plant sprayed with a blank formulation. The results are presented in Table IV.

TABLE III

PLANT MATERIAL USED FOR WHOLE PLANT SCREEN

| Species | Code | Variety | Growth Stage at Treatment | No. Plants per 3" pot | Compost Type |
|---|---|---|---|---|---|
| Barley | BR | Atem | 1–1½ leaves | 4 | JIP* |
| Maize | MZ | Earliking | 2¼–2½ leaves | 1 | PEAT |
| Apple | AP | Red Delicious | 4–5 leaves | 1 | JIP* |

*John Innes Potting compost

TABLE IV

| Plant Material | Effect | | | |
|---|---|---|---|---|
| | R | G | A | 1 |
| BR | 1 | | | 1 |
| AP | 3 | 1 | | 3 |
| MZ | 1 | | 2 | 1 |

KEY
R = Retardation
G = Greening effect
A = Apical damage
I = Interligular or internodal length reduction
All effects are scored visually on a 1–3 basis where
1 = 10–30%
2 = 31–60%
3 = 61–100%
Blank means less than 10% effect

EXAMPLE 10

This Example illustrates the insecticidal properties of compound 1.

The activity of the compound was determined using mite and insect pests. The compound was used in the form of a liquid preparation containing 500 parts per million (ppm) by weight of the compound. The preparation was made by dissolving the compound in acetone and diluting the solution with water containing 0.1% by weight of a wetting agent sold under the trade names "SYNPERONIC" NX until the liquid preparation contained the required concentration of the product. "SYNPERONIC" is a Registered Trade Mark.

The test procedure adopted with regard to each pest was basically the same and comprised supporting a

TABLE II

| COMPOUND NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATOES) |
|---|---|---|---|---|---|---|---|
| 1 | 4 | 4 | 4 | 4 | 3 | 4 | 3 | number of the pests on a medium which was usually a host plant or a foodstuff on which the pests feed, and treating either or both the pests and the medium with the preparation. The mortality of the pests was then assessed at periods usually varying from one to seven days after the treatment.

The results of the tests are given in Table VI as a grading of mortality designated as 9, 5 or 0 wherein 9 indicates 80–100% mortality, 5 indicates 50–79% mortality and 0 indicates less than 50% mortality.

In Table VI the pest organism used is designated by a letter code and the pest species, the support medium or food, and the type and duration of test is given in Table V.

The knockdown properties of Compound 1 against *Musca domestica* was demonstrated as follows.

A sample of Compound 1 was diluted with 2 mls acetone and made up to a 2000 ppm solution with 0.1% aqueous synperonic solution. The solution (1 ml) was then sprayed directly onto twenty mixed sex houseflies held in a drinking cup. Immediately after spraying the cups were inverted and left to dry. An assessment of knockdown was made when the cups were righted 15 minutes later. The flies were then provided with a 10% sucrose solution on a cotton wool pad, and held for 48 hours in a holding room conditioned at 25° C. and 65% relative humidity before a mortality assessment was made.

TABLE VI

| Compound No. | Rate (ppm) | TU$_C$ | MD$_C$ | MD$_K$ | DB |
|---|---|---|---|---|---|
| 1 | 500 | 9 | 9X | 9X | 9 |

X means all insects affected

We claim:

1. A compound of the formula (V):

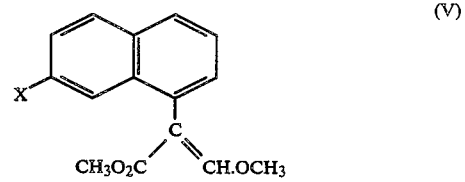

in which X is phenyl, unsubstituted or substituted with one or more of halogen, $C_{1-4}$ alkyl, $C_{1-4}$ alkoxy, phenyl, nitro and cyano.

2. A compound according to claim 1 in which X is phenyl.

3. A compound according to claim 1 in which X is phenyl substituted with one or more of halogen, $C_{1-4}$ alkyl, $C_{1-4}$ alkoxy, phenyl, nitro and cyano.

4. A composition comprising as an active ingredient from 0.005% to 95% by weight of a compound according to claim 1 and an acceptable diluent or carrier therefor.

5. A method of combating fungi which comprises applying to a plant, to a seed of a plant or to the locus of the plant or seed, an effective amount of a fungicidal compound according to claim 1.

6. A method of killing or controlling insect and mite pests which comprises administering to the pest or a locus thereof an effective amount of a compound according to claim 1.

* * * * *

TABLE V

| CODE LETTERS | TEST SPECIES | SUPPORT MEDIUM/ FOOD | TYPE OF TEST | DURATION (DAYS) |
|---|---|---|---|---|
| TU$_E$ | *Tetranychus urticae* (spider mites - eggs) | French bean leaf | Contact | 3 |
| DB | *Diabrotica balteata* (rootworm larvae) | Filter paper/ maize seed | Residual | 3 |
| MD$_C$ | *Musca domestica* (houseflies - adults) | Cotton wool/ sugar | Contact | 1 |
| MD$_K$ | *Musca domestica* (houseflies - adults) | Inverted cup | Knockdown | 2 |

"Contact" test indicates that both pests and medium were treated and "residual" indicates that the medium was treated before infestation with the pests.